United States Patent [19]
Randle

[11] Patent Number: 4,778,268
[45] Date of Patent: Oct. 18, 1988

[54] VISUAL ACCOMMODATION TRAINER-TESTER

[75] Inventor: Robert J. Randle, Sunnyvale, Calif.

[73] Assignee: The United States of America as represented by the Administrator of the National Aeronautics and Space Administration, Washington, D.C.

[21] Appl. No.: 827,185

[22] Filed: Feb. 6, 1986

Related U.S. Application Data

[63] Continuation-in-part of Ser. No. 526,741, Aug. 26, 1983, abandoned.

[51] Int. Cl.$^4$ .............................................. A61B 3/00
[52] U.S. Cl. ..................................... 351/203; 351/237
[58] Field of Search ............... 351/200, 203, 237, 239, 351/243

[56] References Cited

U.S. PATENT DOCUMENTS 4,408,846 10/1983 Balliet ................................. 351/203

OTHER PUBLICATIONS

Randle, Volitional Control of Visual Accommodation, Conf. Proc. No. 82, Adaptation and Acclimatisation in Aero Space Medicine, Germany 9/1970.

Primary Examiner—Rodney B. Bovernick
Assistant Examiner—P. M. Dzierzynski
Attorney, Agent, or Firm—Darrell G. Brekke; John R. Manning; Charles E. B. Glenn

[57] ABSTRACT

The invention is an apparatus for training of the human visual accommodation system. Specifically, the apparatus is useful for training a person to volitionally control his focus to his far point (normally infinity) from a position of myopia due to functional causes. The functional causes could be due, for example, to a behavioral accommodative spasm or the effects of an empty field. The device may also be used to measure accommodation, the accommodation resting position and the near and far points of vision. The device comprises a number of optical elements arranged on a single optical axis (74). Several of the elements are arranged in order on a movable stage (20) in fixed relationship to each other: a light source (30), a lens (32), a target (36), an aperture (42), (48) or (52) and second lens (58). On base (18) and in fixed relationship to each other are eyepiece (70) and third lens (64). Stage (20) generates an image (72) of target (36) and the stage is movable with respect to base (18) by means of knob (22). The device is utilized for the various training and test functions by following a series of procedural steps, and interchanging the apertures as necessary for the selected procedure.

24 Claims, 2 Drawing Sheets

VISUAL ACCOMMODATION TRAINER-TESTER

ORIGIN OF THE INVENTION

The invention described herein was made by an employee of the United States Government and may be manufactured and used by or for the Government for governmental purposes without the payment of any royalties thereon or therefor.

This application is a continuation-in-part of abandoned U.S. patent application Ser. No. 06/526,741, filed Aug. 26, 1983.

BACKGROUND OF THE INVENTION

The present invention relates to a method and apparatus for training and measuring a human visual accommodation system. Accommodation is the automatic adjustment of the eye for seeing at different distances and is accomplished mainly by changes in the convexity of the crystalline lens. Specifically, the apparatus comprises a training aid for teaching subjects to volitionally control the ciliary neuro-muscular system which changes the shape of the crystalline lens to focus a sharp image on the retina of the eye and to improve visual performance by more accurate focusing. It is also capable of measuring the accommodation resting position, the visual near and far points, and may be used as a vision research tool.

DESCRIPTION OF PRIOR ART

A normal or emmetropic eye will focus light rays from a distance on the retina of the eye by means of summated refractions by the several surfaces of the cornea, the fluids of the eye, and the crystalline lens. Light rays emanating from a distant object (beyond about 20 feet) are considered to be parallel (plane wave). With nearer objects, however, the light rays diverge from the object and must be converged to form a clear image on the retinal receptors. Additional refraction of the rays to converge the light is provided by the mechanism of accommodation and is achieved through alteration of the curvature of the anterior lens surface by action of the ciliary neuro-muscular system so that retinal focus is obtained.

There are many situations where keen distant vision is very important. For example, it is necessary for all pilots to be able to perceive the existence of other aircraft in the airspace immediately ahead of their aircraft. Military pilots need to be able to detect other aircraft and identify them as friend or foe at the farthest distance possible. These tasks are interfered with when viewing at high altitude in featureless skies by the phenomenon known as "empty field myopia" in which, without visual targets in the field of view, the accommodation system regresses to its resting position—on the average, less than one meter in front of the eyes—without the observer being aware of it. The resting position is hypothesized to be a position of equilibrium between the sympathetic and para-sympathetic branches of the autonomic nervous system controlling the ciliary muscles (see Owens, D. A., *The Resting State of the Eyes*, Am. Scientist, 72, 378–387, 1984).

It has been shown that, through training in volitional control of accommodation, the tendency for focus to regress to the resting position can be overcome (see Randle, R. J., *Volitional Control of Visual Accommodation*, Conf. Proc. No. 82 on Adaptation and Acclimatization in Aerospace Medicine, AGARD/NATO, Garmisch-Partenkirchen, Germany, September 1970.) Training methods also have potential significant therapeutic value in retraining myopic (nearsighted) individuals (see Trachtman, J. N. *Biofeedback of Accommodation to Reduce Functional Myopia: A Case Report*, A. J. Optom. & Physiol. Optics, 55:400–406, 1978.

In addition to the above described training programs, various other methods and apparatus have been proposed heretofore for measuring, testing and/or improving the performance of a human visual accommodation system. For example, an apparatus for projecting the real image of a pinhole aperture in the eye entrance pupil plane of a subject's eye is disclosed in an article entitled *Ocular-Focus Stimulator* by M. D. Crane and T. N. Cornsweet, J. Opt. Soc. Amer., 60(4):557, 1970.

An exemplary prior art far point extender is disclosed in U.S. Pat. No. 3,843,240 wherein a defocused flashing source of light is viewed through a pinhole aperture (outside of the eye) to produce extension of the eye's accommodation power. U.S. Pat. No. 1,475,698, issued to Henker, shows an apparatus for the objective measurement of the refractive value of the principal point of the eye. In U.S. Pat. No. 3,602,580 there is a disclosure which pertains to a method and apparatus for simultaneously refracting both eyes of a patient wherein a narrow beam of light is directed into each eye at a point spaced from the optical axis of the eye. An optometer of the Scheiner type is revealed in U.S. Pat. No. 1,235,170 issued to Thorner. In U.S. Pat. No. 4,408,846 to Balliet, a standard Badal optometer principle is used to provide visual acuity training using line gratings as visual stimuli. It has no artificial pupil capability, only a distal field stop capability at the distance of the Badal lens. It therefore has no capability for disengaging the accommodation system from its retinal blur/ciliary neuro-muscular reflex arc and to provide open-loop training independent of target blur. The Balliet disclosure also does not teach a method for use of the instrument in measuring the resting position of accommodation, a significant contributor to visual performance. It teaches the use of the instrument to improve visual acuity only.

Objective optometers that usually use infra-red light reflected from the retina and that are usually complex and difficult to use are described in the following publications: Campbell, F. W. and Robson, J. G., *High-Speed Infrared Optometer*, J. Opt. Soc. Amer., 49(3):268–272, 1959. Warshawsky, J., *High Resolution Optometer For The Continuous Measurement Of Accommodation*, J. Opt. Soc. Amer., 54(3):375–379, 1964. Cornsweet, T. N. and Crane, H. D., *Servo-Controlled Infra-red Optometer*, J. Opt. Soc. Amer., 60(4):548–553, 1970. van der Wildt, G. J. and Bouman, M. A., *An Accommodometer: An Apparatus for Measuring the Total Accommodation Response of the Human Eye*, Applied Optics, 10(8):1950–1971, 1971. Wilson, D.C., *Dynamic Optometer*, J. Opt. Soc. Amer., 64(2):235–239, 1974. Kruger, P. B., *Infrared Recording Retinoscope for Monitoring Accommodation*, Amer. J. Optom. & Physiol. Optics, 56(2):116–123, 1979. Lovasik, J. V., *A Simple Continuously Recording Infrared Optometer*, Amer. J. Optom. & Physiol. Optics, 60(1):80–87, 1983.

SUMMARY OF THE INVENTION

In view of the foregoing, a need is apparent for a simple device to train one to overcome empty field myopia and to provide therapy for behavioral myopia.

If training human visual accommodation for better visual performance is ever to have wide application and become a real social benefit, a really practical, simple and inexpensive device must be provided. Accordingly, an object of the present invention is a device that is economical to fabricate, simple to operate, maintain and transport and that will:

1. Image artificial pupils in the human eye entrance pupil plane;
2. Provide training of a human visual accommodation system using the visual feedback of a Scheiner artificial pupil pair;
3. Provide for measuring the trainee's resting position using a single artificial pupil and the Scheiner artificial pupil pair in an alternating fashion;
4. Allow measurement of the near and far points by using a third artificial pupil of large diameter (8.0 mm or more) so that accommodation operates with a natural eye entrance pupil size and reacts to defocus blur as it normally and naturally does;
5. Promote further research using the above described capabilities to more fully understand the operation of the visual accommodation system, particularly its functioning independent of its parent system that is provided by the ability to image a distal aperture inside the eye at the precise location of the physiological entrance pupil plane.

Another object of the present invention s a method of training a human visual accommodation system which is based on the use of tiny (0.3 to 0.5 mm) artificial pupils imaged in the eye entrance pupil plane of the trainee. These tiny pupils so increase the trainee's depth of focus that accommodation is not required because targets at all distances are in clear focus as in a pinhole camera. This frees accommodation from the retinal blur reflex (called the open-loop mode) and allows its functioning to be controlled by other factors, e.g. conscious control. When only a single tiny pupil is used the trainee has no feedback as to whether he is at the same focus distance as the target, and the accommodation system, without a blur signal to process, regresses to its natural resting position. On the other hand, when two tiny apertures are used side-by-side (called a Scheiner aperture or Scheiner pair) the trainee sees a double image of the target when his focus distance is not the same as the target and a single image when his focus distance is the same as the target. He thus has visual feedback of his state of focus and an indication of which direction he must adjust his accommodation to attain conjugacy of his retina and the viewed target if he is out of focus.

Thus, in accordance with the above objects, there is provided an apparatus comprising a stationary base with a movable stage mounted on one end of the base. Five elements are mounted on the movable stage and maintain a fixed relationship to each other: a light source mounted at one end of the stage; a first lens mounted next to the light source to focus the light rays; a transilluminated target mounted at the middle of the stage; a second lens mounted at the opposite end of the stage; and a plurality of apertures mounted on the stage at the primary focal plane of the second lens between the second lens and the target. The light from each aperture selected for use, emanating from the aperture position at the focal plane of the second lens, is collimated by that second lens. An eyepiece is mounted on the opposite end of the base, and a third lens is mounted on the base between the eyepiece and the second lens. The third lens receives the collimated light of the apertures from the second lens and, no matter what the distance between the second and third lenses, brings this light to a focus in a real image at its secondary focal plane, made to coincide with the eye entrance pupil plane by positioning the eye with the eyepiece. A real image of the target placed two focal lengths from the second lens between the aperture plane and the first lens is formed two focal lengths on the opposite side of the second lens between the second lens and the third lens. The light emanating from the target passes through the aperture but, since it does not originate at that plane, is not collimated by the second lens as is the light emanating from the apertures. This real image of the target is fixed in relationship to the second lens and all elements mounted on the movable stage. It thus moves with movement of the stage and presents a movable visual target for the Badal lens and, thus, the eye. As is well known, the accommodative power required at the eye position one focal length to the left of the Badal lens to focus the target through this lens is a direct and linear function of the distance of the target from that lens on the opposite side of the eye.

Succintly, the optical configuration of the present invention provides for the seemingly contradictory results of fixing an artificial pupil in the entrance pupil plane of the eye notwithstanding movement of the stage and providing for corresponding movement of the Badal lens target for all movement of the stage.

BRIEF DESCRIPTION OF THE DRAWINGS

The above and other objects, features and advantages of the invention will be more fully understood from the following detailed description of the accompanying drawings in which.

DETAILED DESCRIPTION OF THE INVENTION

Figure 1:
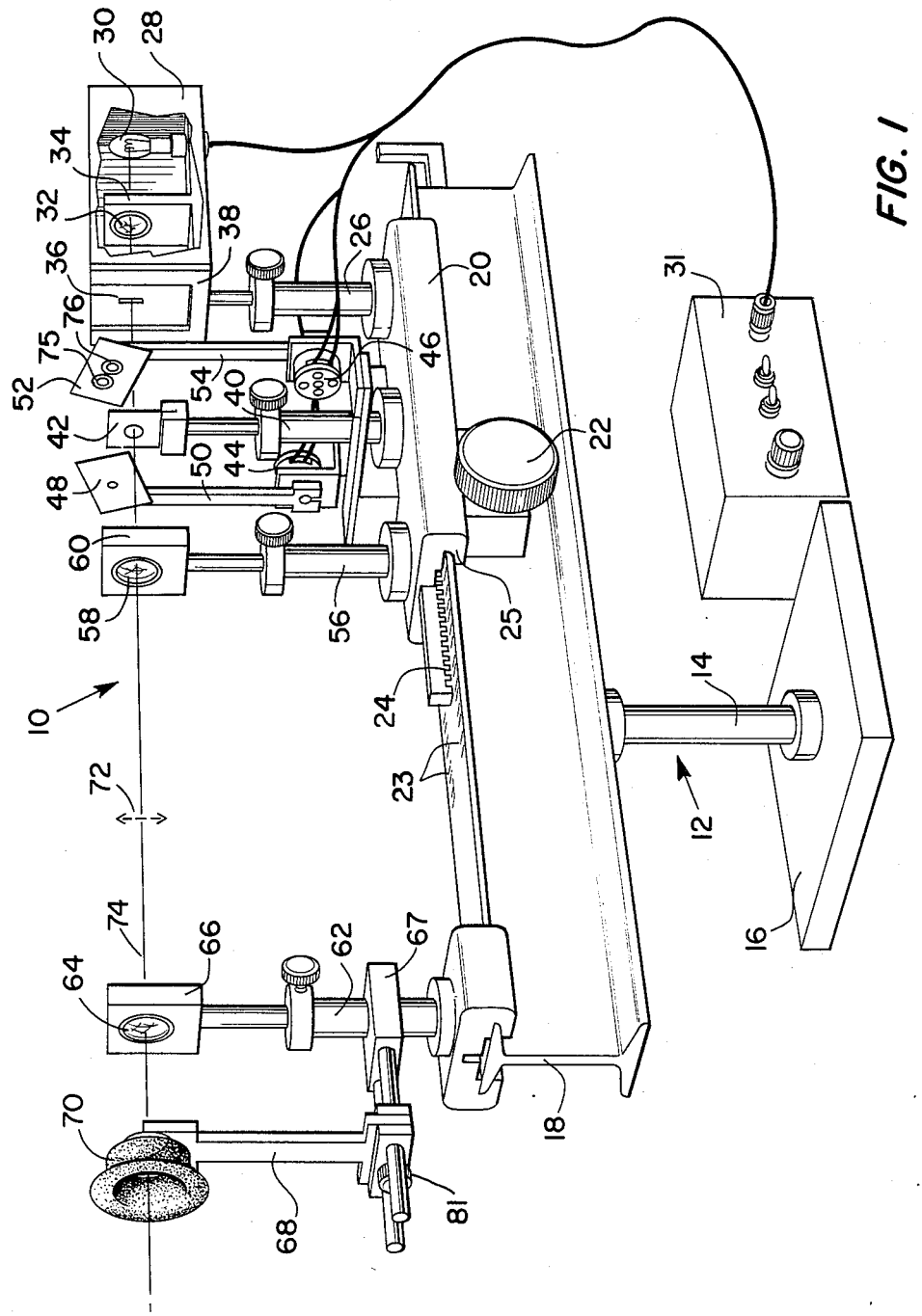
FIG. 1 is a perspective view of an embodiment of the invention.

FIG. 1 shows an embodiment of the invention designated generally by the numeral 10. In the center of the figure is shown a stand 12 having a rod 14 extending upward vertically from a plate member 16. Attached to the top of stand 12 is a base plate or rail 18. Mounted on one end of base plate 18 is a movable stage 20 which is driven by means of a rack 24 and pinion gear (not shown). Rotatable knob 22 is coupled to the pinion gear. Stage 20 may be moved toward or away from eye piece 70 and lens 64 on base plate 18 by rotating knob 22 clockwise or counterclockwise.

A diopter and/or distance scale 23 is affixed to base plate 18 adjacent to rack 24 as, for example, by etching or painting. Scale 23 is read by using the edge 25 of stage 20 as a pointer. Stage 20 may also be driven by a suitable servo system and controlled by a simple digital computer with an analog to digital converter, as will be obvious to those skilled in the art. Thus, the invention can be fully automated as a teaching machine. Scale reading, feedback to the trainee and trainer, data recording, and data processing can all be automated.

A number of elements of the invention are all mounted on movable stage 20 in fixed relationship to each other. Vertically adjustable rod 26 affixed to stage 20 supports rectangular box 28 which contains a light source 30 and a first lens 32 mounted in holder 34. a target 36 is situated on end 38 of box 28. The target may transmit light therethrough from light source 30 with the area adjacent thereto being opaque or vice versa. End 38 of box 28 may be, for example, a photographic transparency with a desired image centrally positioned. As will be obvious to those skilled in the art, the transparencies may be sine or square wave (line) gratings for the measurement and training of visual acuity performance or they may be any visual stimuli of which a photographic or other transparency may be made.

Mounted on vertically adjustable stand 40 adjacent to target 36 is a fixed "wide open" aperture 42 which is 8.0 mm or more in diameter. The aperture is positioned so that the optical axis 74 of lenses 32, 58 and 64 passes centrally therethrough. Apertures 48 and 52 supported by pivotable arms 50 and 54, respectively, may be moved onto the optical axis 74 by means of high speed solenoids 44 and 46, respectively. Aperture 48 is a "pinhole" aperture with an orifice 0.3 to 0.5 mm in diameter. Aperture 52 is a "Scheiner" aperture having two orifices 0.3 to 0.5 mm in diameter separated laterally 1.0 to 2.0 mm along an horizontal line (called variously "Scheiner pair", two pinhole aperture, double orifice, double aperture, two pinhole Scheiner). When solenoid 46 is activated aperture 52 is moved to the position where the optical axis 74 bisects the two orifices. Apertures 42, 48 and 52 are not depicted to scale in FIG. 1.

When the device is in use, there is either one aperture on the optical axis (42) or two (42 and 48 or 42 and 52). As it is intended that aperture 42 be larger than aperture 48 or aperture 52, there is only one effective aperture on the optical axis at any given time (the smaller one).

A switching circuit 78 (see FIG. 2) housed in control box 31 energizes solenoids 44 and 46.

Specifically, the switching circuit 78 provides these selectable modes of operation:

1. The energization of solenoid 44 to move aperture 48 to the optical axis 74. The de-energization of solenoid 44 to remove aperture 48 from the optical axis 74.

2. The energization of solenoid 46 to move aperture 52 to the optical axis 74. The de-energization of solenoid 46 to remove aperture 52 from the optical axis 74.

3. The automatic alternate energization and de-energization of the solenoids so that apertures 48 and 52 are alternately on optical axis 74. In this mode, it is preferable that the switching circuit include a user-selectable timing circuit so that the "on-axis" interval of aperture 52 may be selected by the practitioner. Typically, aperture 52 is in place for a period which is less than the time of the latent period of the accommodation response, 0.25 to 0.35 seconds.

Control box 31 also houses a power supply to provide power to lamp 30. The switching functions of control box 31, including varying the brightness of the visual target, may also be performed by a simple digital computer as will be obvious to those skilled in the art.

The orifice of Scheiner aperture 52 may be covered with different colored filters 75 and 76, respectively. These filters may be, for example, red and green. These filters provide a cue for the direction of defocus because each of the two images provided by the Scheiner aperture will have a different color and will change places laterally as the defocus changes from too much eye lens power to too little eye lens power.

On the end of stage 20 is mounted a vertically adjustable stand 56 with second lens 58 and lens holder 60.

Figure 2:
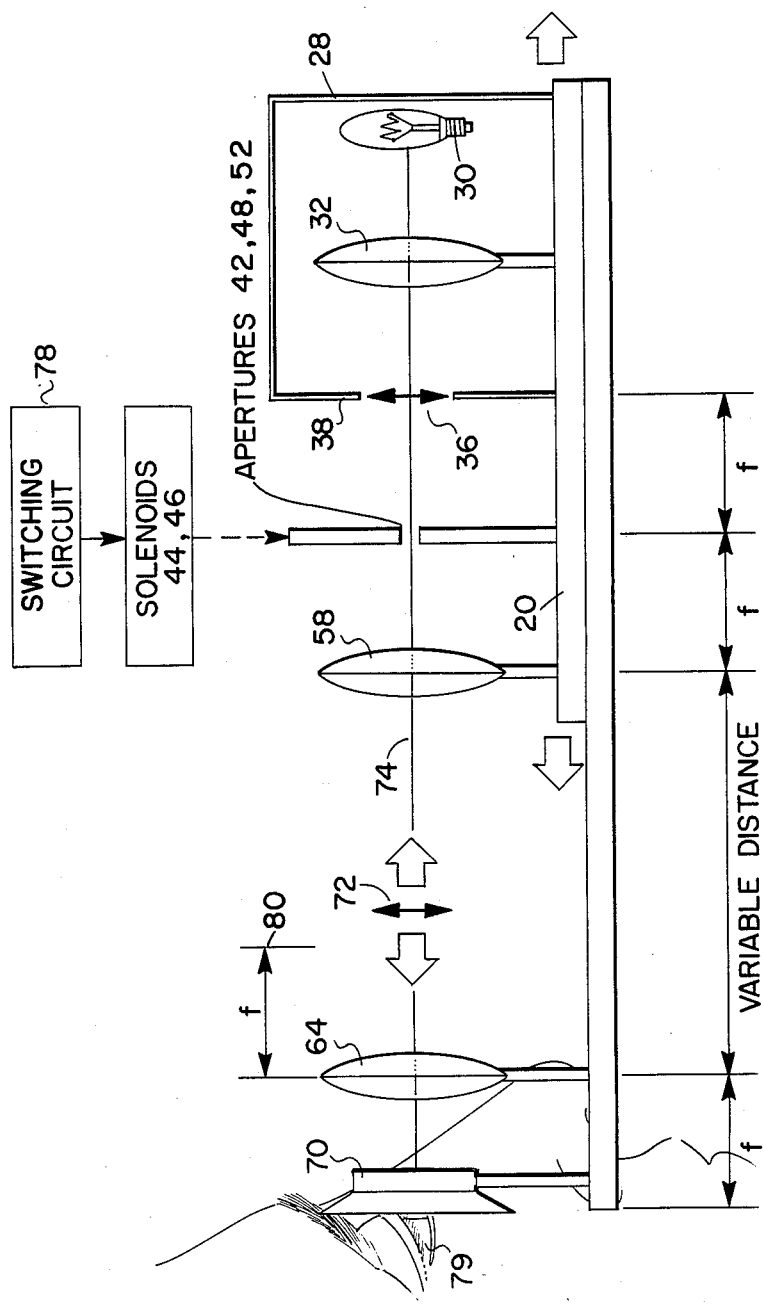
FIG. 2 is a schematic drawing of a side view of the optical train of FIG. 1 showing the elements of the invention and their relative locations on a fixed base and movable stage. Also shown is an image of a target

On the end of rail 18, proximal to the eye, 79 is FIG. 2, is a vertical adjustable stand 62 which supports lens holder 66 and third lens 64. Also attached to stand 62 is a bracket 67 supporting eyepiece 70.

FIG. 2 shows the preferred spacing of certain items in the trainer tester. Lamp 30 is spaced one focal length from lens 32 so that lens 32 directs most of the light parallel to the optical axis 74. Back-lighted, arbitrary target 36 is a fixed distance from second lens 58. This distance is twice the focal length (f) of lens 58. Light from target 36 passes through apertures 42, 48 or 52 and is not collimated by lens 58. Instead, lens 58 forms a real image of target 36 two focal lengths on the other, left, side of lens 58. Of course, as stage 20 is moved with respect to base 18 by means of knob 22, image 72 is moved the same distance with respect to stationary third lens 64. This real image 72 of the target 36 is the stimulus target for the eye 79 as it views the target through the Badal lens 64. The movement of real image 72 changes the dioptric power (lens power) required by the eye 79, viewing it through lens 64, to keep it in clear focus. The closer real image 72 is to lens 64 the more accommodative power is required by the eye at eyepiece 70 to keep it in clear focus. This is the accommodation stimulation and measurement aspect of the invention.

The three apertures 42, 48 and 52 placed at the aperture plane are one focal length (f) from lens 58. It is well known that light emanating from objects placed at the focal plane of a lens will be collimated by the lens. The light coming from apertures 42, 48 or 52 is thus collimated but not the light that has emanated from target 36 and is passing through these apertures. The collimated light from apertures 42, 48 or 52 travels forward in a plane wave form without convergence or divergence until it impinges upon lens 64. There, lens 64, by the principle of optical conjugacy, refocuses the collimated image of the apertures at its own focal plane in a real image. Because the image is collimated and its light rays are without convergence or divergence while travelling between lenses 58 and 64, a change of distance between lenses 58 and 64 cannot change the location of the image of the apertures located one focal length to the left of lens 64 in FIG. 2.

Adjustment knob 81 in FIG. 1 is used to position each individual eye so that the entrance pupil of each eye is located at the focal plane of lens 64. This places the eye entrance pupil and the real image of apertures 42, 48 or 52 in exact correspondence. This position of the eye is necessary to make lens 64 function as a Badal optometer and it is necessary for the use of apertures 42, 48 or 52 as true artificial pupils.

Since the aperture in use is imaged and fixed exactly in the natural entrance pupil plane of the eye, the field stop of the system is this artificial pupil. This optical relay system is unique in that, as far as field of view is concerned, it is as though the eye were viewing the visual target from the position of the apertures, in which case the field of view is that of the eye with whatever aperture is in place as an artificial pupil. what is seen by an eye entrance pupil placed at the position of the apertures on stage 20 is also what is seen by an eye entrance pupil placed at eyepiece 70 no matter which of the three apertures 42, 48 or 52 is being used (when the natural pupil of the eye decreases in size the amount of light entering the eye is decreased, but the field of view is little affected). The remaining, practical, limitation on field of view is the diameter of the lenses used in the optical train, lenses 58 and 64.

The several modes of operation of the apparatus will now be described. This will further clarify the function of the optical elements discussed above.

Measurement of the Far Point of Vision

The visual far point (punctum remotum) is defined in the Dictionary of Visual Science, Schapero, M. et al., Chilton Co., Phila., N.Y., 1960, as:

The conjugate focus of the retina (fovea) when the accommodation s relaxed or at its minimum. In emmetropia, the far point is said to be at infinity; in myopia, it is at some finite distance in front of the eye; in hyperopia, it is at some finite (virtual) distance behind the eye.

What needs to be determined, therefore, is the optical distance from the subject's eye at and beyond which the image or target 36 can no longer be kept in focus, i.e., when accommodation is fully extended in distance. If the point at which the image can no longer be kept in focus is between lens 64 and the focal plane 80 of lens 64, the far point is closer than infinity and the eye is said to be myopic or "near-sighted". On the other hand, if the point is behind focal plane 80 (to the right of plane 80 in FIG. 2), the far point is said to be hyperopic (hypermetropic) or "far-sighted". If the point is right at the focal plane 80, the eye is then deemed emmetropic or normal.

For the measurement of the far point of vision, the subject is preferably seated in front of device 120 with the entrance pupil plane of one eye placed one focal length to the left of lens 64 using eyepiece 70. The lamp 30 is illuminated and the wide-open aperture 42 is in place on optical axis 74. The image of aperture 42 is fixed in the eye entrance pupil plane but the effective aperture is the natural pupil of the subject since it is the smaller of the two. This allows the accommodation system to operate in a natural fashion. An image of target 36 is found at 72. This image is the object for lens 64 and the eye. The position of stage 20 is determined by the rotation of knob 22 which in turn determines the position of the subject's stimulus, 72, with respect to lens 64.

To start the measurement process, the stimulus is initially placed by the examiner between lens 64 and focal plane 80. This requires the subject to exert some accommodative effort, an amount that is dependent upon where the stimulus has been placed with respect to lens 64. A diopter scale 23 imprinted on base 18 (proximal end of stage 20) enables the measurement of the dioptric power required at the eye to focus the stimulus (image 72). The subject rotates knob 22 to move the stimulus toward focal plane 80 and stops the movement when the stimulus first appears to blur. The dioptric power is read off the scale and recorded. Because of high variability in biological response systems, it is preferable to measure the far and near points by approaching them from both directions and then taking the average reading after several trials. That is, the subject moves the stimulus away from lens 64 from a near position set by the examiner until the stimulus blurs and the examiner reads the scale. Then the subject moves the stimulus from a far position selected by the examiner towards lens 64 until the blurring of the stimulus stops and the examiner reads the scale. This blurring and clearing is repeated for as many times as is deemed appropriate by the examiner and an average value of the doptric distance is computer. This mean dioptric distance is the refractive error of the eye under test and, when converted into distance, is the monocular far point of vision of that eye under these test conditions, with the natural pupil as the effective entrance pupil.

Measurement of the Near Point of Vision

The dictionary cited above defines the accommodative near point of vision (punctum proximum) as:

The point representing the maximum dioptric stimulus to which the eye can accommodate. Hence, usually the nearest point anteriorly on which the eye can focus.

The measurement process for determining the near point of vision is similar to measuring the far point. Again, the large aperture 42 is used to allow accommodation to operate and it remains fixed in place at the eye entrance pupil plane as stage 20 is moved in the measurement process. The examiner, using knob 22, places the stimulus between lens 64 and focal plane 80. The subject then uses knob 22 to move stage 20 and stimulus 72 toward him thus increasing the accommodative power required at the eye at eyepiece 70 to focus the stimulus. When the stimulus first starts to blur, the subject stops the movement of the stage 20 and the examiner notes where the pointer has stopped on scale 23. The bracketing procedure used above is also preferably employed here. In accordance with that procedure, the examiner places the stimulus close to lens 64 such that it is too close to be focused and will be observed as blurred. The subject then moves the stage 20 away from him until the stimulus first appears in focus. When the movement is stopped, the examiner reads scale 23. This blurring and clearing (approaching and receding stimulus) procedure is repeated as many times as is considered necessary by the examiner and a mean value of the several scale reading is calculated. This average value of accommodation, when converted to distance from diopters, is the monocular near point of vision of that eye under these test conditions, with the natural pupil as the effective entrance pupil.

Measurement of the Resting Position of Accommodation

Normally a defocused image is a blurred image. However, there are two optical techniques employed in which a defocused target is not seen as blurred no matter how great the lack of conjugacy between the retina and the viewed target. One of these is the use of an artificial pupil that is significantly smaller than the smallest natural pupil. This, as in the familiar pinhole camera, provides a very large depth of focus or range over which adjustment of accommodation is not required to keep the target in clear focus. Another way to accomplish this is to use two pinhole apertures placed side-by-side and bisecting the optical axis. Since very small apertures are used, again, the defocused target will also be seen as in clear focus for all target positions. However, for all cases where the retina and the viewed object are not optically conjugate, two images of the target will be seen. Unlike the single aperture, it is obvious to the observer when his accommodation is not conjugate to the target. Since this visual feedback is without blur, the accommodation system is not stimulated and the subject is free to try to gain focus—bring the two images into a single image—using his own conscious, volitional control. The subject can even be given information as to which way to control his focus by use of color filters over each of the Scheiner apertures. The two images will change positions as the subject's focus passes through the point of conjugacy, where the image is single. The single pinhole aperture and the double pinhole aperture are used in measuring the resting position using the invention.

When the eye has a great depth of field or views a visual field that is without targets or has very ill-defined targets, the eye reverts or regresses to its resting position. The resting position has been shown to be at an average intermediate focus distance of about 1.5 diopters—a little over two feet—and not at infinity as classically thought (see Owens, op. cit.). This phenomenon, also called empty field, dark field, night, twilight, and anomalous myopia, is an unconscious process. It varies widely in magnitude from individual to individual. Its measurement provides the clinician or researcher with important insight into the accommodation dynamics of the person under test or investigation.

In the measurement of the resting position the eye is made to settle to its resting position by removing the defocus blur retinal stimulus. By rotating knob 22, target 72 is placed at a distance from lens 64 that has a dioptric distance from the eye that is equal to the subject's previously measured far point. The subject focuses on this target to start. Then pinhole aperture 48 is placed on optical axis 74 by means of solenoid 44 from whence it is imaged and fixed in the eye entrance pupil plane. This so increases the depth of focus that no stimulus blur is apparent and target 72 is merely a fixation point for the eye. The eye not under test is covered with a patch. The subject is allowed a reasonable amount of time for accommodation to settle at its resting position (at least one minute). After this period, solenoid 44 is de-energized moving aperture 48 off of the optical axis and aperture 52 is moved thereon by energization of solenoid 46. After an interval shorter than the accommodation latency period, about 250 milliseconds (0.250 secs), aperture 52 is removed from the optical axis and aperture 48 is returned to it. During the brief period that aperture 52 is on the optical axis, the eye under measurement will see either a single image or the double image indicating that the eye is not conjugate to the far point target. If it is the first, then the resting position coincides with the far point; if it is the second, then the eye has drifted to a new position of focus, towards a resting position that is different from the far point.

At repeated regular intervals, aperture 52 is alternated with aperture 48 for its brief exposure. The exposure of the double image is made shorter than the latency of accommodation to avoid an unconscious attempt on the part of the subject to fuse the two images volitionally and thus yield a spurious measure of the resting position. As the alternation occurs, the subject is directed to move stage 20 with knob 22 in a direction that will cause the double image to be made single. When the two images are superimposed and stage 20 is brought to rest, the pointer for scale 23 indicates the resting position of the subject's eye. As with the measurement of the near and far points, this procedure may be repeated several times to calculate a more stable measure of the subject's resting position.

Training Visual Accommodation

The subject invention has some salient features that make it suitable for training visual accommodation to respond to volitional control. Some of these are the direct result of the ability of the invention to image remote apertures within the eye at the entrance pupil plane and to have them remain fixed there as the apparatus changes the position of the visual stimulus. The salient features are:

1. It can open the accommodation reflex loop, i.e., it removes defocus blur and allows volitional control to be brought into play. When the single tiny aperture is used the loop is opened without feedback; when the two tiny pupils are used the loop is opened with visual feedback.

2. It can provide a defocus cue that is not normally available in real world visual tasks and that is easily and unambiguously interpreted as a form of visual feedback. The defocus double image provided by the Scheiner artificial pupil is not itself a trigger for the accommodation reflex.

3. It allows accommodation to be decoupled from binocular vergence by using only one eye, thus limiting it to a more pure accommodation response. Since willed control is initiated in higher neural centers than at each individual eye and, since there is strong consensuality between the two eyes, both eyes will respond to training a single eye.

An example of training a myope (near-sighted) to extend his far point will be given. For this training, aperture 52 is placed on optical axis 74 and an image of the Scheiner aperture pair is fixed within the eye at the entrance pupil plane for all positions of real image 72. Two exercises are given the trainee (out of many possible, as will be obvious to those skilled in the art) to demonstrate to the trainee that he can control his own focus response and to develop an initial skill in so doing.

1. A target is placed at an arbitrary but visually clear position for the trainee by the trainer using knob 22 to position real image 72 at an appropriate distance from Badal lens 64. The trainee sees a single image of the visual target. The trainer then abruptly moves the visual target to a new position and the trainee sees the target abruptly split into a double image. The instructions to the trainee are to attempt to bring the images back together using his own volitional control. When the trainee has fused the images, the trainer abruptly moves the target back to its original position and the trainee is again instructed to fuse the newly doubled image. This is repeated until there is little or no delay in the fusing of the two images by the trainee when the trainer abruptly moves the target to a new postion.

2. With the apparatus in the same configuration as it was for the first exercise, the trainer again sets a visual target in a position where it will be comfortably in focus for the trainee. He then instructs the trainee to try to make the single Scheiner image into a double image by volitionally focusing nearer than the target. When he has achieved the double image he is instructed to return it to a single image. When he can do this reasonably quickly, the trainer sets the target at a comfortable close dioptric distance and the trainee is now instructed to volitionally focus farther than the target, double the image, and then return it to a single image.

After some practice with exercises like these, the trainee is given training in extending his far point in very small steps. The procedure is the following. The trainee's far point is measured using the method described above. The trainer then sets the visual target beyond that dioptric value by 0.2 diopter using knob 22 to position real image 72 the appropriate distance from Badal lens 64. Aperture 52 is placed on the optical axis by energizing solenoid 46. The trainee sees a double image when he first looks into the eyepiece and then tries, using volitional control, to make the image single and achieve clear focus on the target at the new far point. When the trainee has achieved a single image, solenoid 46 is de-energized and aperture 52 is instantaneously removed. Aperture 42 is now the effective aperture and the effective artificial pupil, the retinal blur reflex loop is now closed, and the target will be seen by the trainee as clear, without defocus blur. The trainee is asked to hold the target clear for 60 seconds after which time the visual target is moved outward in dioptric distance another 0.2 diopter, aperture 52 is returned to the optical axis, and training continues. If, however, when the reflex loop is closed by aperture 52 is returned to the optical axis 74 and the trainee continues to try to fuse the double image.

After some practice trainees can learn how to merge and separate the Scheiner images. It is not known how this is done nor have previous trainees been able to verbalize what they do to control their focus. It is known, however, that when individuals are told that they can control their own focus and are given training or even allowed to practice on their own in an ad lib fashion, they gain control over this visual function (see Cornsweet, T. N. and Crane, H. D., *Training The Visual Accommodation System*, Research Note, Vision Research, 13:713–715, 1973 and Randle, op. cit., 1970).

The functions herein described as being performed by a trainer or an implied monitor can be automated by mounting stage 20 on a servo motor and using a simple digital computer with analog to digital conversion as a process controller, as will be obvious to those skilled in the art.

Potential Invention Configuration

To enhance the training and make it possible for the subject to alternately view the real world objects and stimulus 72 without leaving the eyepiece 70, a 50/50 beamsplitter may be added to the invention. When the beamsplitter is added, the eyepiece is rotated 90 degrees so that its viewing axis is orthogonal to optical axis 74. The beamsplitter is placed where the two axes intersect. Thus, the subject may either look through the beamsplitter at the real world or look on the beamsplitter for stimulus 72. When operated thusly, neither eye is occluded, binocular viewing is in force, and binocular accommodation is measured. The components of the instrument need not be supported on a tall stand or on a base as large as 18. The instrument may be repackaged in a much smaller volume. It is possible, for instance, to helmet mount the device for dynamic studies in driving cars, in piloting aircraft, operating computer terminals, and other human engineering investigations without intervention in the ongoing visual task.

The advantage of the invention over present day devices is that it brings together some optical principles in a uniquely new way (the relayed aperture, fixed artificial pupil and moving stimulus) to meet the need for state of the art instrumentation to explore all dynamic aspects of the newly emerging model of the visual accommodation system: the resting position, regression to rest in impoverished visual worlds, volitional control, the open-loop response, and the malleability of accommodation for training and modification.

While preferred embodiments and several alternative embodiments of the present invention are disclosed, it is contemplated that various other modifications may still be made thereto without departing from the spirit and scope of the present invention. Accordingly, it is intended that the scope of the invention be determined by the claims hereinafter provided.

What is claimed is:

1. An apparatus having an optical axis for testing and training a human subject's volitional control over the subject's visual accommodation system using one of the subject's eyes, said eye having a retina and an eye entrance pupil plane, comprising:

means for providing a target;

means for projecting a real image of said target a selected dioptric distance from said retina;

means for providing a pair of apertures with one of said apertures being located on each side of said optical axis;

means for fixing a real image of said pair of apertures in said eye entrance pupil plane, each of said apertures having a diameter such that said real image of said target appears to said subject through said real image of said apertures in said eye entrance pupil plane as being in focus; and means for selectively changing the magnitude of said dioptric distance of said real image of said target from said retina such that when said retina and said real image of said target are conjugate said real image of said target appears to said subject as a single real image of said target and when said retina and said real image of said target are not conjugate said real image of said target appears to said subject as a pair of real images of said target.

2. An apparatus having an optical axis for testing and training a human subject's volitional control over the subject's visual accommodation system using one of the subject's eyes, said eye having a retina and an eye entrance pupil plane, comprising:

means for providing a target;

means for projecting a real image of said target a selected dioptric distance from said retina;

means for selectively changing the magnitude of said dioptric distance of said real image of said target from said retina;

first means for fixing a real image of a single wide-open aperture having a first predetermined diameter in said eye entrance pupil plane such that when said retina and said real image of said target are conjugate said real image of said target appears to said subject to be in focus and when said retina and said real image of said target are not conjugate said real image of said target appears to said subject to be out of focus;

second means for fixing a real image of a single pinhole aperture having a second predetermined diameter in said eye entrance pupil plane such that when said retina and said real image of said target are conjugate said real image of said target appears to said subject to be in focus and when said retina and said real image of said target are not conjugate said real image of said target appears to said subject to still be in focus;

third means for fixing a real image of a pair of Scheiner apertures, each having a third predetermined diameter in said eye entrance pupil plane such that when said retina and said real image of said target are conjugate said real image of said target appears to said subject to be in focus as a single real image of said target and when said retina and said real image of said target are not conjugate said real image of said target appears to said subject to still be in focus, but as a pair of real images of said target; and means for selectively positioning said pinhole and Scheiner apertures on said optical axis covering said wide-open aperture.

3. An apparatus according to claim 2 wherein said positioning means comprises means for selectively positioning said pinhole and Scheiner apertures on said optical axis in a predetermined order and for predetermined intervals of time.

4. An apparatus according to claim 3 wherein said positioning means comprises a solenoid means coupled to each of said pinhole and Scheiner apertures.

5. An apparatus according to claim 2 wherein said positioning means comprises means for selectively positioning said pinhole and said Scheiner apertures on said optical axis alternately and for a first and a second interval of time, respectively; and said changing means comprises means which can be operated by a subject to change said dioptric distance if and until said pair of real images of said target observed when using said Scheiner apertures merge into a single real image of said target to obtain the dioptric distance of the natural resting position of the subject's eye.

6. An apparatus according to claim 5 wherein said first interval of time during which said pinhole aperture is used is long enough for the subject's visual accommodation system to settle at its resting position and said second interval of time during which said Scheiner apertures are used is shorter than the accommodation latency period of said subject's eye.

7. An apparatus according to claim 2 wherein said first diameter is at least 8.0 mm, said second and third diameters are approximately 0.3 to 0.5 mm and said Scheiner apertures are separated laterally from approximately 1.0 to 2.0 mm.

8. An apparatus according to claim 2 wherein each of said Scheiner apertures comprises a different color filter.

9. An apparatus according to claim 2 comprising an eyepiece and a Badal lens and wherein said dioptric distance changing means comprises means for mounting said target and said single wide-open, single pinhole and Scheiner apertures on a movable stage for moving said target and apertures relative to said eyepiece and Badal lens.

10. An apparatus for testing and training a human subject's volitional control over the subject's visual accommodation system using one of the subject's eyes, said eye having a retina, an eye entrance pupil plane and an accommodation latency period comprising:
a visual light source;
a first lens;
a second lens having a focal plane;
a third lens having a focal plane;
a target which in use is transilluminated by said light source located between said first and said second lenses;
an eyepiece for fixing the position of said eye entrance pupil plane at said focal plane of said third lens;
a plurality of apertures;
means for selectively placing said apertures on the optical axis of said second lens midway between said second lens and said target at the focal plane of said second lens so that in use a visual real image of said apertures is fixed in said eye entrance pupil plane; and
means for moving in unison said light source, said first lens, said second lens, said target and said plurality of apertures relative to said third lens and said eyepiece for moving a projected visual real image of said target relative to said retina without moving said real image of said apertures from said eye entrance pupil plane.

11. An apparatus according to claim 10 wherein said plurality of apertures comprises a wide-open aperture having a first predetermined diameter, a pinhole aperture having a second predetermined diameter, and a pair of Scheiner apertures, each having a third predetermined diameter.

12. An apparatus according to claim 11 wherein said first predetermined diameter is at least 8.0 mm and said second and third predetermined diameters are approximately from 0.3 to 0.5 mm.

13. A method of testing and training a human subject's volitional control over the subject's visual accommodation system using one of the subject's eyes, said eye having a retina and an eye entrance pupil plane, comprising the steps of:
providing a target;
projecting a real image of said target a selected dioptric distance from said retina;
providing a pair of apertures with one of said apertures being located on each side of said optical axis;
fixing a real image of said pair of apertures in said eye entrance pupil plane, each of said apertures having a diameter such that said real image of said target appears to said subject through said real image of said apertures in said eye entrance pupil plane as being in focus; and
selectively changing the magnitude of said dioptric distance of said real image of said target from said retina such that when said retina and said real image of said target are conjugate said real image of said target appears to said subject as a single real image of said target and when said retina and said real image of said target are not conjugate said real image of said target appears to said subject as a pair of real images of said target, thereby providing the subject the opportunity to volitionally merge the two retinal images together thus making the retina and said real image of said target conjugate.

14. A method of measuring the resting position and testing and training a human subject's volitional control over the subject's visual accommodation system using one of the subject's eyes, said eye having a retina and an eye entrance pupil plane, comprising the steps of:
providing a target;
projecting a real image of said target a selected dioptric distance from said retina;
selectively changing the magnitude of said dioptric distance of said real image of said target from said retina;
fixing a real image of a single wide-open aperture having a first predetermined diameter in said eye entrance pupil plane such that when said retina and said real image of said target are conjugate said real image of said target appears to said subject to be in focus and when said retina and said real image of said target are not conjugate said real image of said target appears to said subject to be out of focus;

fixing a real image of a single pinhole aperture having a second predetermined diameter in said eye entrance pupil plane such that when said retina and said real image of said target are conjugate said real image of said target appears to said subject to be in focus and when said retina and said real image of said target are not conjugate said real image of said target appears to said subject to still be in focus;

fixing a real image of a pair of Scheiner apertures, each having a third predetermined diameter in said eye entrance pupil plane such that when said retina and said real image of said target are conjugate said real image of said target appears to said subject to be in focus as a single real image of said target and when said retina and said real image of said target are not conjugate said real image of said target appears to said subject to still be in focus, but as a pair of real images of said target; and selectively positioning said pinhole and Scheiner apertures on said optical axis covering said wide-open aperture.

15. A method according to claim 14 wherein said positioning step comprises the step of selectively positioning said pinhole and Scheiner apertures on said optical axis in a predetermined order and for predetermined intervals of time.

16. A method according to claim 15 wherein said positioning step comprises the step of providing a solenoid means coupled to each of said pinhole and Scheiner apertures.

17. A method according to claim 14 wherein said positioning step comprises selectively positioning said pinhole and said Scheiner apertures on said optical axis alternately and for a first and a second interval of time, respectively; and said changing step comprises the step of providing a means which can be operated by a subject to change said dioptric distance if and until said pair of real images of said target observed when using said Scheiner apertures merge into a single real image of said target to obtain the dioptric distance of the natural resting position of the subject's eye.

18. A method according to claim 17 wherein said first interval of time during which said pinhole aperture is used is long enough for the subject's visual accommodation system to settle at its resting position and said second interval of time during which said Scheiner apertures are used is shorter than the accommodation latency period of said subject's eye.

19. A method according to claim 14 wherein said first diameter is at least 8.0 mm, said second and third diameters are approximately 0.3 to 0.5 mm and said Scheiner apertures are separated laterally from approximately 1.0 to 2.0 mm.

20. A method according to claim 14 wherein each of said Scheiner apertures comprises a different color filter.

21. A method according to claim 14 wherein said apparatus comprises an eyepiece and a Badal lens and wherein said dioptric distance changing step comprises the step of providing a means for mounting said target and said single wide-open, single pinhole and Scheiner apertures on a movable stage for moving said target and apertures relative to said eyepiece and Badal lens.

22. A method of testing and training a human subject's volitional control over the subject's visual accommodation system using one of the subject's eyes, said eye having a retina, an eye entrance pupil plane and an accommodation latency period comprising the step of:

providing a visual light source;

providing a first lens;

providing a second lens having a focal plane;

providing a third lens having a focal plane;

providing a target which in use is transilluminated by said light source located between said first and said second lenses;

providing an eyepiece for fixing the position of said eye entrance pupil plane at said focal plane of said third lens;

providing a plurality of apertures;

selectively placing said apertures on the optical axis of said second lens midway between said second lens and said target at the focal plane of said second lens so that in use a visual real image of said apertures is fixed in said eye entrance pupil plane; and moving in unison said light source, said first lens, said second lens, said target and said plurality of apertures relative to said third lens and said eyepiece for moving a projected visual real image of said target relative to said retina without moving said real image of said apertures from said eye entrance pupil plane.

23. A method according to claim 22 wherein said plurality of apertures comprises a wide-open aperture having a first predetermined diameter, a pinhole aperture having a second predetermined diameter, and a pair of Scheiner apertures, each having a third predetermined diameter.

24. A method according to claim 23 wherein said first predetermined diameter is at least 8.0 mm and said second and third predetermined diameters are approximately from 0.3 to 0.5 mm.

* * * * *